United States Patent [19]

Trost

[11] Patent Number: 5,651,890

[45] Date of Patent: Jul. 29, 1997

[54] USE OF PROPANE AS STRIPPER GAS IN ANAEROBIC DIGESTION OF WASTEWATERS

[76] Inventor: Paul B. Trost, 1010 10th St., Golden, Colo. 80401

[21] Appl. No.: 714,010

[22] Filed: Sep. 13, 1996

Related U.S. Application Data

[63] Continuation-in-part of Ser. No. 416,142, Apr. 4, 1995, abandoned.

[51] Int. Cl.[6] ............................................. C02F 11/04
[52] U.S. Cl. ........................... 210/603; 210/613; 210/631
[58] Field of Search ........................ 210/603, 605, 210/612, 613, 631

[56] References Cited

U.S. PATENT DOCUMENTS

| | | | |
|---|---|---|---|
| 3,242,071 | 3/1966 | Walker | 210/14 |
| 3,383,309 | 5/1968 | Chandler | 210/11 |
| 4,198,292 | 4/1980 | Snider | 210/12 |
| 4,289,625 | 9/1981 | Tarman | 210/603 |
| 4,311,593 | 1/1982 | Benjes | 210/603 |
| 4,372,856 | 2/1983 | Morrison | 210/603 |
| 4,482,458 | 11/1984 | Rovel | 210/603 |
| 4,511,370 | 4/1985 | Hunziker | 48/197 |
| 4,655,924 | 4/1987 | Heijnen | 210/603 |
| 4,714,796 | 12/1987 | Senkan | 585/328 |
| 4,780,415 | 10/1988 | Ducellier | 435/166 |
| 4,826,600 | 5/1989 | Ely | 210/603 |
| 4,897,195 | 1/1990 | Erickson | 210/603 |
| 4,983,297 | 1/1991 | Kaczmarek | 210/605 |
| 5,015,384 | 5/1991 | Burke | 210/603 |
| 5,037,551 | 8/1991 | Barkley | 210/603 |
| 5,116,506 | 5/1992 | Williamson | 210/610 |
| 5,185,079 | 2/1993 | Dague | 210/603 |
| 5,232,596 | 8/1993 | Castaldi | 210/603 |
| 5,298,163 | 3/1994 | Ehlinger | 210/603 |
| 5,310,485 | 5/1994 | Roshanvaran | 210/603 |

FOREIGN PATENT DOCUMENTS

| | | |
|---|---|---|
| 241999 | 1/1991 | European Pat. Off. . |
| 2484990 | 4/1992 | France . |

OTHER PUBLICATIONS

Finney, C.D., and Evans, R.S., Anaerobic Digestion—the Rate Limiting Process and the Nature of Inhibition, Science, vol. 190, p. 1088, (1975).
Butane–Propane News, Jan. 1996 (p. 32).
Methane Production From Waste Organic Matter, Stafford et al, CRC Press (1980).

*Primary Examiner*—Neil McCarthy
*Assistant Examiner*—Theodore M. Green
*Attorney, Agent, or Firm*—Dorr, Carson, Sloan & Birney, P.C.

[57] ABSTRACT

Anaerobic digestion of wastewaters can be made more effective by introducing propane gas from an external source therein in order that the propane gas strips gas produced by the anaerobic digestion (e.g., methane, carbon dioxide, etc.) from the biomass system.

13 Claims, 1 Drawing Sheet

USE OF PROPANE AS STRIPPER GAS IN ANAEROBIC DIGESTION OF WASTEWATERS

RELATED APPLICATIONS

This patent application is a continuation-in-part application of my U.S. patent application 08/416,142 entitled "Use of $C_2$ to $C_6$ Gases in Anaerobic Digestion of Wastewaters" filed on Apr. 4, 1995, abandoned.

BACKGROUND OF THE INVENTION

1. Field of the Invention

Wastewater "biomass" systems normally consist of a mixture of water, organic matter and a variety of bacterial genera whose food, to a large degree, consists of the organic matter component of the biomass and/or other organic waste materials. Anaerobic digestion is widely employed to reduce biomass and/or to treat high (>1000 mg/l) biological oxidation demand (BOD) liquid wastewaters. Progressive destruction of the organic matter in biomass systems also has been made more efficient by introducing various gases that serve as nutrients for bacteria and/or to strip gas molecules such as those of methane, carbon dioxide, ammonia, hydrogen, hydrogen sulfide, etc. from the microbial solutions where such gases occur as waste products during bacterial degradation. Nitrogen, hydrogen and recirculated biomass product gases (e.g., carbon dioxide, methane and hydrogen) have been used for these purposes.

2. Description of Related Art

Anaerobic digestion processes have been utilized to treat and remove organic compounds from waste products such as sewage, sewage sludge, chemical wastes, food processing wastes, agricultural residues, animal wastes and other organic waste materials such as those produced by paper pulping plants. Anaerobic bacteria (or other anaerobic microorganisms) require a virtual absence of oxygen in order to digest organic waste materials. Hence, anaerobic digestion reactors are tightly sealed to prevent entrance of air therein. This airless condition is often referred to in the literature as an "anoxic" condition.

Anaerobic digestion may be carried out in a single reactor chamber or in multiple reactor chambers (e.g., those having two or more physically distinct chambers in which two or more distinct operations are independently carried out). Heat is often added to such reactors in order to maintain adequate temperatures for certain thermophilic or mesophilic bacteria that digest or otherwise breakdown the organic components of a biomass. Mixing of incoming wastes or biomass within such reactors, either by mechanical agitation, or by gas bubbling, also is commonly used to accelerate a wide variety of such anaerobic digestion processes.

The products of anaerobic digestion normally consist of: (1) a gas phase containing carbon dioxide, methane, ammonia, small amounts of certain other gases e.g., hydrogen sulfide and hydrogen (and trace amounts e.g., less than one tenth of one percent by volume) of other gases such as propane), which, in total, constitute what is commonly referred to as "biogas"; (2) a liquid phase (aqueous in nature) in which ammonia, nutrients and a host of organic gases and inorganic chemicals are dissolved; and (3) a colloidal phase of suspended solids containing undigested organic and inorganic compounds, synthesized biomass and/or bacterial cells.

It also has been long recognized that low anaerobic gas product concentrations within an anaerobic reactor can result in significantly reduced reactor detention times and thus smaller reactor size requirements. Reduction of reactor size, in turn, results in the advantages of reduced capital costs, as well as reduced operating costs. Some workers in this art also have postulated that maintenance of low gas product concentrations serves to increase overall anaerobic treatment efficiencies. They reason that: if the outer surfaces of bacterial cell walls are not covered with gas molecules, this condition will allow newly produced gas molecules to leave such bacteria more quickly—and thereby produce more efficient digestive processes. Moreover, these relatively "gas-bubble-free" bacteria cell walls will permit secondary addition of nutrient molecules into such bacteria (through their cell walls) owing to the fact that the outer cell wall surfaces are not occluded by the presence of gas molecules. These conditions also are thought to cause generation of greater amounts of methane, carbon dioxide, ammonia, hydrogen, etc. gases, and, hence, ultimately produce cleaner liquid effluents that, in turn, can be disposed of more economically. It also should be noted that increased digestion efficiencies result in reduced solids concentrations within the effluent products of such processes. This circumstance serves to reduce the quantity of solid or semi-solid material that must be ultimately transported to a disposal site. Finally, higher treatment efficiencies render the solid and liquid effluents of such processes more amenable to separation of potentially valuable resources (heavy metals and nutrients such as nitrogen-containing ammonia) that may be contained in such effluents.

The degradation of organic matter present in anaerobic systems proceeds by many highly complex chemical processes. Their final stages usually involve processes that result in production of several gases: methane, carbon dioxide, ammonia, hydrogen sulfide and trace amounts of other gases including propane. For example, anaerobic treatment of municipal wastewater ultimately produces a biogas consisting mostly of methane ($CH_4$) and carbon dioxide ($CO_2$) along with a sludge product. In these larger anaerobic digestion plants, the biogas byproduct is often burned to provide heat for the digester and/or for local energy production devices. Biogas, however, in and of itself, does not burn particularly well since it has a relatively low BTU value of about 650 BTU/ft$^3$. Consequently, in order to burn biogas, expensive burner modifications must be made. Moreover, the biogas usually has to be mixed with other, better burning, fuel gases in order to most effectively burn the biogas component of a biogas/fuel gas mixture.

At least three separate stages have been distinguished in anaerobic processes. They can take place in separate chambers of a digester, or they can take place simultaneously in a milieu wherein various microbial genera coexist with organic matter in various stages of degradation. In any case, the first stage of such anaerobic digestion processes takes place when solid complex organic materials such as cellulose, proteins, lignins and lipids are hydrolyzed into simpler, soluble organic molecules such as fatty acids, alcohols, carbon dioxide and ammonia. Such digestion processes also may be aided by extracellular enzymes (i.e., enzymes operating outside of the microbial cells of the biomass) that usually produce pyruvic acid, lactic acid, acetic acid, propionic acid or butyric acid.

The second stage of anaerobic digestion processes, often called "acetogenesis", involves conversion of the fatty acid products of the first stage to acetic acid, propionic acid, hydrogen, carbon dioxide and other low molecular weight organic acids. This stage is carried out by so-called acetogenic bacteria.

The third stage of such digestive processes primarily involves methanization process in which residual metabolites of the preceding two steps are converted into methane by methanogenic bacteria. To this end, at least two distinct bacteria species are employed. One group converts hydrogen and carbon dioxide to methane while a second group converts acetate to methane and bicarbonate (carbon dioxide in solution). Both groups of bacteria are however anaerobic in character. Thus, successful digestion requires a balance between production and consumption of various intermediate materials in each of the three stages of anaerobic digestion.

Those skilled in this art also will appreciate that a "rate-limiting" stage in such processes is that stage in which conversion of such waste materials is the slowest. Both Stage 1 and Stage 3 can be rate - limiting in anaerobic digestion processes. For example, in the first stage of certain anaerobic digestion processes, the breakdown of certain complex organics such as cellulose (e.g., those from paper pulping operations) to organic fatty acids is the most inherently slow step—even though the microorganisms that provide the enzymes to catalyze this particular breakdown grow relatively quickly. This follows from the fact that a lignin component in pulp waste products prevents access of such enzymes to their cellulose component and thereby slowing digestion of these complex organics. Other complex organics simply do not biodegrade easily; consequently, long retention times and low loading rates are needed for their conversion in this step. Consequently, the presence of such complex organics usually implies that Stage 1 will rate limit certain anaerobic digestion processes.

By way of comparison, conversion of organic fatty acids to organic volatile acids (primarily acetic acid) in Stage 2 is generally much easier and, consequently, Stage 2 is rarely the rate limiting step of an anaerobic process. In other words, the organisms needed for Stage 2 usually grow fast, and quickly break down the fatty acid intermediates in the biomass. On the other hand, the third stage is usually much slower than the second. This follows from the fact that methane-forming bacteria normally grow relatively slowly and are much more sensitive to various environmental factors compared to the microorganisms that carry out Stages 1 and 2. Indeed, reactions of methane-forming bacteria are usually "the rate-limiting reaction" in most anaerobic reaction systems. Hence, the third stage is usually considered the overall rate-limiting stage of most anaerobic digestion processes. Consequently, the goal of most industrial and/or environmental protection anaerobic digestion processes is to maintain, at the highest level possible, without sacrificing overall process stability, a rate of "food" consumption and production for the microorganisms of the rate-limiting, third stage.

Next, it should be noted that many anaerobic biomass systems also contain ammonia and/or hydrogen sulfide gases. Their presence is known to inhibit the purifying operations of many organic material-containing wastewater/biomass systems. For example, it is known that during the second stage of many anaerobic digestion processes, hydrogen sulfide-reducing bacteria frequently residing in such biomass systems may consume a large proportion of the volatile fatty acids—to the detriment of this second, or acetogenic, stage, and, hence, to the detriment of the desired production of acetic acid. This results in higher proportions of volatile fatty acids escaping the degradation process. Sulfate-reducing bacteria also are known to be harmful to the third stage: firstly, because they consume hydrogen and carbon dioxide to the disadvantage of the methanogens, and secondly, because the hydrogen sulfide produced by such sulfate-reducing bacteria inhibits the function of various acetoclastic bacteria in many such systems. Analogous, but usually less severe, inhibitions are known to occur as a result of the presence of various other gases (e.g., methane, ammonia, carbon dioxide, etc.) produced by anaerobic digestion of various organic material-containing wastewaters. Thus, all of these facts and circumstances indicate that the inhibition phenomena associated with the presence of various gas products of anaerobic digestion processes (e.g., methane, ammonia, carbon dioxide, hydrogen sulfide, etc.) can be greatly diminished by rapidly removing these gases from the digestive process—and most preferably from the most sensitive stage thereof, the third, or methane production, stage.

Many academic, industrial and patent references have recognized one or more of the above-noted gas inhibition problems and have suggested various solutions to them. For example, within the academic and industrial literature, the following articles are particularly instructive: FinLey, C. D., and R. S. Evans, Anaerobic Digestion—the Rate Limiting Process and the Nature of Inhibition, Science, 1975, Vol. 190, p. 1088; McCarty, P. L., Anaerobic Waste Treatment Fundamentals, Part I, Public Works, 1964, p. 107 and Obayashi, A. W., and J. M. Gorgan, Management of Industrial Pollutants by Anaerobic Processes in Industrial Waste Management Series, W. James (ed.), Lewis Publishers, Inc., Chelsea, Mich., 1985.

FinLey and Evans reported that a "fourth" rate controlling step may be present in anaerobic digestion—namely a step based upon the fact that dissolved gas products (e.g., $CH_4$+$CO_2$) must undergo a transfer from the liquid to the gas phase. That is to say that, even though most investigators consider the third step (i.e. biological conversion of organic acids, such as acetic and propionic acid into methane and carbon dioxide) to be the rate controlling reactions, Finney and Evans proposed that a fourth step i.e., transfer of dissolved gases from the liquid phase to a gas phase or, alternately, the rate of removal of these gas bubbles away from bacterial cell walls, is actually the rate limiting step in anaerobic digestion.

To prove their hypothesis, Finhey and Evans conducted controlled anaerobic digestions under the presence of both increased agitation and, more importantly, under vacuum conditions. The presence of a vacuum resulted in a lowering of the partial pressure of $CH_4$ and $CO_2$ above the liquid. By lowering the partial pressure above the liquid, the concentration of dissolved $CH_4$ and $CO_2$ in the liquid phase was also lowered. Thus the bacterial degradation products of $CH_4$ and $CO_2$ clinging to microbial cell walls were more rapidly transferred away from those cell walls into a aqueous phase and ultimately out of the system. When they compared their reaction rates to established and well documented reaction rates by other workers, Finney and Evans observed that their vigorous agitation and lower pressure conditions resulted in a 600% increase in the reaction rate. They attributed this increased reaction rate to the faster removal of $CH_4$ and $CO_2$ bubbles away from the bacterial cell walls thereby effectively increasing the "bacterial surface area available for permeation processes." In other words the bacteria had more surface area available to allow intake of their food sources of acetic and propionic acids.

Those skilled in this art, however, also will appreciate that application of a strong vacuum (e.g., 100 Torr) such as that employed by Finney and Evans, in a commercially sized digester, may create operating problems due to vessel collapse and/or foaming conditions that tend to be created by such vacuum conditions. For example, this problem was noted by Keenan, C. W. and Wood, J. H., 1967, General College Chemistry, 3rd Ed., Harper & Row, NY. 814 p. (242).

It also should be noted in passing that the Finhey and Evans gas stripping concept and experimental evidence is supported by the chemical principle established by LeChatelier in 1885 (LeChatelier's Principle) which states that "when a stress is brought to bear on a chemical system at equilibrium, the system tends to change so as to relieve the stress." Therefore, for the reaction of

if C and/or D are removed from the system then more A+B are converted to C+D.

As applied to anaerobic digestion, the following system may be conceptualized:

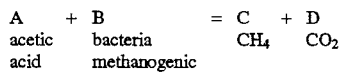

Thus if $CH_4$ and $CO_2$ are removed from an anaerobic system (i.e., "stress" is applied to the system), additional acetic acid will be consumed by the bacteria in order to re-establish equilibrium conditions. Another way of looking at LeChatelier's principle in the context of anaerobic digestion, is that no living system, no matter how simple, enjoys being forced to reside in its own waste products.

Application of LeChatelier's principle was therefore well demonstrated by the experimental work of Finney and Evans (1975), including their application of a vacuum that resulted in more rapid removal of $CH_4$ and $CO_2$ from their experimental system and thereby allowing the methogenic bacteria to consume more acetic (and propionic) acid, and thereby increasing their overall reaction rates. These authors recognized that microbial growth could be inhibited by absorption of toxic compounds onto the surface of cells and thereby affecting cell wall permeability to gases and/or dissolved feed passing either into, or out of, such cells. They also noted that as $CH_4$ and $CO_2$ are produced by bacteria and migrate through a cell wall on a molecular basis, they tend to remain attached to the cell wall pending their "escape" into the aqueous solution. In any case, Finney and Evans proposed that by remaining attached to the cell wall these product gases may effectively decrease the surface area of the bacteria, inhibit cell permeability and reduce a cell's capability of absorbing needed nutrients.

The academic literature also has long recognized that some trace amounts of propane are produced by anaerobic digester systems. For example, a leading text in this general area: Methane Production From Waste Organic Matter, by Stafford et al., CRC Press, Inc., Boca Raton, Fla. (1980) ("the Stafford reference") states (on page 114) that some "small quantities" of propane may be formed by "polymerization" of methane in an anaerobic digester. It also might be noted that Stafford et al. also state that anaerobic digesters usually make 60–70% methane and 30–40% $CO_2$ along with "small amounts" of $H_2S$ and $H_2$.

The patent literature also has long recognized the fact that certain gases can be used to "strip" various gases (e.g., methane, carbon dioxide and hydrogen sulfide) from anaerobic biomass systems. The patent literature also has well recognized use of certain gases as nutrients for various microorganisms residing in anaerobic digestion systems. For example, U.S. Pat. No. 4,289,625 (the '625 patent) teaches use of a "hybrid, bio-thermal" system comprised of an anaerobic digester unit and a thermal gasifier unit. This patent teaches that various gases produced by heating a solids component (sludge) of a biomass system in a thermal gasifier unit can be re-introduced into the system's anaerobic digester unit. This system seeks to "provide a process for high conversion of carbonaceous material in biological feed stocks to gas products" (column 2, lines 39 and 40). It also should be noted that this reference teaches that the thermal gasifier unit produces 94 mole percent methane (column 8, line 58). In effect, the anaerobic digester system of the '625 patent achieves greater methane production per unit of feed by "digesting" and "cracking" the anaerobic sludge material and, secondarily, by feeding the thermal gasifier's, gaseous products ($H_2$, CO), back to the digester unit as food sources for the microorganisms residing therein. Some of these gaseous products are characterized as "$C_xH_y$" in the '625 patent, but no particular emphasis is laid upon a propane gas component that may fall within the highly generalized term "$C_xH_y$"—especially since a thermal gasifier will produce an extremely varied source of hydrocarbons due to its "cracking" ability.

The '625 patent acknowledges that the act of recycling product gases that "principally contain methane and carbon dioxide", "may inhibit methane production due to mass action" (column 1, lines 52–58) i.e., the '625 patent's recognition of Le Chattier's principal in its processes. It might also be noted that no mention is made in the '625 patent of any deleterious affects to the rate of methane production due to "mass action". Nor does the '625 patent teach or suggest introduction of a soluble gas (such as propane) which is not a food source for the bacteria; nor does the '625 patent teach introduction of a soluble gas into its digester unit to achieve a beneficial effect on the rate of methane production therein. The importance of the distinction between the "rate" of biogas production versus the total "amount" of biogas production will be more fully developed in the later descriptions of applicant's processes. For the moment, however, suffice it to say that applicant's processes seek to increase the rate of biogas production relative to the rates of biogas production achieved by processes such as those described in the '625 patent. It also should be noted at this point that, by way of contrast with the '625 patent, applicant's process does not seek to provide "higher methane production per unit of feed", but rather accelerated rates of digestion.

With respect to the subject of "stripping" gases from anaerobic systems, many patent references teach processes for stripping free hydrogen sulfide content of an anaerobic digester. This removal of hydrogen sulfide may take place either by starting with a germination gas or by starting with a treated effluent leaving a digestion reactor. The patent literature also has recognized that, after removal of hydrogen sulfide, the purified effluent may be partially recycled back to the reactor. In such processes, acid formation, sulfate reduction and methanogenesis usually all take place, simultaneously, within a single reactor unit.

U.S. Pat. No. 5,037,551 teaches bubbling oxygen-enriched gas through a first digestion zone and a low-molecular-weight alkane through a second zone of an anaerobic digester.

U.S. Pat. No. 4,198,292 teaches increased yield of anaerobic digestion by placing a slight vacuum over the biomass system.

U.S. Pat. No. 4,655,924 teaches use of microorganism carrier materials in digester systems.

European Patent EP-0,241,999, describes an anaerobic fermentation based upon successively passing an effluent through two fixed-culture reactors. Acetification takes place in the first reactor. This is coupled with biological reduction of any sulfates present. The effluent leaving the first reactor is then freed of hydrogen sulfide gas by stripping it by means of an inert gas in an intermediate structure before the effluent enters a second reactor. The pH of this system is maintained between 6.5 and 6.7 to promote both sulfate reduction and hydrogen sulfate stripping.

U.S. Pat. No. 5,298,163 teaches that a "neutral" gas (no disclosures are made as to the exact identity of such "neutral" gas) can be introduced in a biodegration process in order to strip or otherwise displace hydrogen sulfide gas from a biomass system.

U.S. Pat. No. 5,015,384 teaches an anaerobic digestion process that employs an injection of "anoxic" gases to strip carbon dioxide gas from the system so that its pH remains neutral or nearly so. This reference states: "The primary requirement is that the gas be anoxic, i.e., not contain oxygen or other constituents toxic to the anaerobic bacteria." This reference does not, however, specifically identify or exemplify the anoxic gases—but it does suggest that carbon dioxide gas bubbles attached to the outer surface of bacteria cell walls may be removed by the overall stripping process described therein.

U.S. Pat. No. 4,826,600 teaches a process for altering the pH of a anaerobic system (e.g., one degrading sewage) by using methane gas to strip carbon dioxide gas from the system. This process may also employ an "inert" gas to aid in the withdrawal of gaseous products. The preferred "inert" gas is methane.

U.S. Pat. No. 3,383,309 teaches a process for anaerobic digestion of sewage sludge in a digester wherein biodegradable solids in a sludge are converted (by a first group of bacteria) into fatty acids. The resulting fatty acids are thereafter transformed into methane gas and gaseous carbon dioxide (by methane and carbon dioxide forming bacteria). The novelty of this process resides in the step of removing the digester gases from the digester, adding energy to at least a portion of these digester gases, cracking them into hydrogen and other gases such as methane, and then introducing at least a portion of the hydrogen gas into the sludge in the digester for assimilation by the methane forming bacteria, with a resultant increase in fatty acid transformation by the bacteria.

U.S. Pat. No. 5,116,506 discloses a method of treating liquid waste. The method includes the steps of (1) providing a reactor having a gas permeable membrane that divides the reactor into a liquid compartment for the liquid waste and a gas compartment for a gas component; (2) providing a biofilm layer on the liquid compartment side of the membrane (the layer comprising a first layer of aerobic organisms adjacent the membrane, and a second layer of anaerobic organisms between the aerobic layer and liquid); (3) introducing an oxygen containing gas into the gas compartment and allowing it to diffuse through the membrane; and (4) introducing a liquid waste into the liquid compartment and allowing it to react with the biofilm layer.

U.S. Pat. No. 5,310,485 teaches an anaerobic wastewater treatment process wherein biogas—generated in a digester unit, and in a flotation container—is recirculated through a gas entrainment system that is positioned away from the flotation container.

U.S. Pat. No. 5,185,079 teaches an anaerobic reactor that removes biogas from the top of the reactor and re-introduces it into the bottom of said reactor. This reference also notes the beneficial effects of applying a vacuum during its settling phase to promote removal of gas bubbles attached to bacterial cell walls.

U.S. Pat. No. 4,780,415 discloses an anaerobic degradation process having certain novel biogas collection and reintroduction steps.

U.S. Pat. No. 4,511,370 teaches a process for utilization of household garbage. It includes the steps of collecting carbon dioxide and methane gas produced by the process, separating them from each other and then re-introducing the methane component of the gas separation back into the process.

U.S. Pat. No. 4,311,593 teaches a process for treatment of wastewater wherein, as the wastewater flows downwardly through a digester unit, methane is released and bubbles to the surface where it is either collected for combustion in an energy production process, or is recirculated. A pressure of about one pound per square inch is kept on the digester in order to keep carbon dioxide dissolved in the system's liquid effluent.

U.S. Pat. No. 4,372,856 discloses a process for anaerobic digestion of waste wherein sludge is sparged with methane gas in order to stimulate the growth of anaerobic bacteria and, thus, greater production of biogas. This reference also teaches that biogas may be stripped of its "undesired" carbon dioxide and hydrogen sulfide components by passing it through a scrubbing liquid prepared by use of ammonia produced by another phase of the overall process.

U.S. Pat. No. 4,482,458 teaches a process for anaerobic treatment of wastewater that includes the steps of collecting a biogas product of the anaerobic treatment, compressing it and then re-introducing the compressed biogas back into the treatment system.

U.S. Pat. No. 3,242,071 teaches a stirring method that is particularly useful in operating a digester.

U.S. Pat. No. 4,897,195 teaches use of rotary digestion modules to produce carbon dioxide, methane and nitrogen based fertilizers by anaerobic digestion of various waste materials.

U.S. Pat. No. 4,983,297 teaches use of an anaerobic treatment for water separated from crude oil.

U.S. Pat. No. 5,232,596 teaches a biodegradation process wherein off-gas components of said process are recirculated back to the bioreactor.

The use of propane in anaerobic digesters is also noted in the trade literature. For example, the January 1996 issue of the trade magazine Butane-Propane News (p. 32) reports that propane can be bubbled through anaerobic digesters to accelerate their reaction rates. The operating parameters of such systems, however, are not disclosed therein.

These academic, trade and patent references suggest that much work has been done to improve the performance of anaerobic digesters—and, indeed, much has been accomplished. However, further improvements in this art are still being sought on many fronts—and are always welcome when, in fact, they are achieved. Applicant's present contribution to this art resides in his finding that when propane gas is injected into anaerobic digestion systems in certain concentrations hereinafter more fully described, anaerobic digestion performance is improved far beyond those levels of improvement achieved by introduction of methane, carbon dioxide or hydrogen stripper gases. The herein described processes also are based upon applicant's recognition that even though many references teach use of certain gases (e.g., methane, carbon dioxide and hydrogen) to strip carbon dioxide and hydrogen sulfide gases from anaerobic systems, the full beneficial effects of removing such gases from anaerobic systems has not been heretofore fully achieved. This failure follows from the fact that large concentrations of certain stripper gases used in many prior art processes produce deleterious, inhibitory effects on the biomass microorganisms due to the principles of operation of Le Chatelier Principle in such anaerobic systems for the reasons previously noted. In effect, applicant's process seeks to circumvent the problems associated with the inhibitory effects of increased methane, carbon dioxide and hydrogen concentrations in anaerobic microorganisms—while still providing a means for stripping gaseous products from the outer cell walls of such microorganisms. Applicant's processes also serve to force gases that are dissolved in the aqueous phase of the biomass out of the overall anaerobic digestion system.

SUMMARY OF THE INVENTION

Applicant shares the Finney and Evans view that the rate limiting step for anaerobic digestion is transfer of bacterial product gases (e.g., $CH_4$ and $CO_2$) away from bacterial cell walls and ultimately out of the system. Hence, applicant also believes that aiding displacement of these gases away from bacterial cell walls, and ultimately out of the aqueous phase of a biomass system, will improve the effectiveness of that system. Indeed, applicant's experimental work supports the Finney and Evans generalized concept that a more rapid removal of $CH_4$ and $CO_2$ from such systems results in faster and more complete reactions which, in turn, result in decreased capital and operating costs for those anaerobic digestion systems employing the herein described processes.

Applicant has found that transfer of $CH_4$ and $CO_2$ away from bacterial cell walls, and ultimately out of the aqueous phase of a biomass system, can be significantly increased by bubbling a propane-containing gas through the biomass in amounts such that the propane concentration in the biogas product of such anaerobic digestion processes reach certain hereinafter prescribed levels. In effect, this propane-containing gas acts as a soluble "stripper gas" rather than as a nutrient. It should also be noted that the propane component of such a gas is not behaving as if it were an "inert" gas in applicant's processes. Indeed, its solubility in anaerobic systems is important to applicant's overall goal of removing methane and carbon dioxide from the cell walls of those microorganisms used to carry out anaerobic digestion. Applicant has found, however, that in order for propane gas to serve as a reaction-rate-improving soluble stripper gas, it must be present in anaerobic biomass systems in concentrations such that the biogas emanating from the biomass liquid phase contains at least 0.5 percent by volume propane gas. It is even more preferred that the propane-containing gas be introduced into the anaerobic digester in amounts such that the biogas given off by the biomass will comprise from about 6 to about 15 volume percent propane.

Those skilled in this art will appreciate that the propane concentrations in the biogas produced by the hereindescribed processes are much greater than the "trace" concentrations (e.g., which are usually less than about 0.1 volume percent of the biogas) of propane found in a "naturally occurring" biogas (i.e., a biogas given off by a biomass into which no propane from an external source has been introduced). Naturally, the propane-containing gas introduced into a biomass of applicant's process must be present in concentrations sufficient to produce the minimum 0.5 volume percent in applicant's biogas. The propane-containing gases from external sources will preferably contain more than one volume percent propane, and more preferably contain more than five volume percent propane, and most preferably contain more than fifty volume percent propane. These propane percentages in the biogas (i.e., more than 0.5 volume percent and preferably between 6 and 15 volume percent) assume that the anaerobic digester is operating on a more or less "continuous" or "steady state" basis rather than on a "batch" basis.

This all goes to say that, since propane is only produced in very small trace amounts by anaerobic digesters (most probably by the polymerization mechanism postulated by the previously cited Stafford reference), the propane needed to produce a biogas having even as little as 0.5 percent propane must come from an "external" (external to the anaerobic digester system) source of propane. In other words since biogas, and especially biogas from anaerobic digesters having no thermal gasifier unit, "naturally" contains considerably less than 0.5 volume percent propane gas, the propane used in applicant's processes must come from sources external to the anaerobic digester system. Obviously, such external propane sources must contain sufficient amounts of propane gas to produce a biogas product having more than 0.5 volume percent propane—and more preferably should contain sufficient amounts of propane to produce a biogas product having from about 6 to about 15 volume percent propane. Applicant also has found that introduction of propane into a biomass in amounts such that the biogas product has more than about 20 volume percent do not appreciably increase the rate of digestion in such anaerobic digestion systems.

To this end, this invention involves injecting propane gas, or a mixture of gases containing a propane gas component (i.e., a propane-containing gas) from an external source, into a biomass undergoing anaerobic digestion in order to "strip" various inhibiting gases (e.g., methane, carbon dioxide, ammonia, hydrogen sulfide, etc. produced by the anaerobic microorganisms e.g., bacteria, methanogens, etc.) residing on the outer surfaces of such microorganisms and/or dissolved in the aqueous phase of the biomass system. This stripping action serves to greatly increase the technical and/or economic efficiency of such anaerobic digestion processes. The "propane gas" and/or "propane-containing mixture of gases" (both of which terms, for the purposes of this patent disclosure, may be taken to mean a "propane-containing gas") introduced (e.g., by sparging) into such an anaerobic digestion biomass systems—for the most part—will be predominantly obtained from an "industrial" source as opposed to being obtained from recycling the biogases naturally produced by the anaerobic digester (or, a la the '625 patent, produced by use of a thermal gasifier used in conjunction with an anaerobic digester unit). That is to say that even though some anaerobic digestion systems may produce trace amounts of propane along with their production of relatively large amounts of methane, carbon dioxide and hydrogen sulfide, these trace amounts of propane are not, in and of themselves, sufficient to produce the effects needed to carry out applicant's processes. Consequently, propane gas from bottled propane gas, industrial products, or industrial by-products will supply most of the propane gas needed for the practice of this invention. By way of example only, industrial waste gases that contain a significant propane gas component (e.g., those comprising at least 1.0 weight percent propane, e.g., those obtained from a petroleum refinery) can be used as the propane gas source in applicant's processes. Relatively "pure" liquid propane gas (LPG) is an even more preferred propane source for the practice of this invention. Those skilled in this art will appreciate that LPG will "flash" when it enters the relatively low pressure conditions existing in such anaerobic reactors. In other words the LPG may enter the reactor as a liquid, but it will then quickly flash to a gaseous form.

Applicant also has found that the efficiency of the herein described processes is, at least in part, due to the solubility of those gases to be removed from anaerobic digestion systems (e.g., carbon dioxide, methane) relative to the solubility of the propane stripper gas when the propane is introduced in amounts sufficient to more or less continuously produce a biogas product that is comprised of at least one percent by volume propane. For example, applicant has found that even though it is reported that the solubility of methane in pure water at 20° C. is 0.4 cc per 100 cc of aqueous solution, and the solubility of propane at 18° C. is 6.5 cc/100 cc, these solubilities are not readily achievable in a biomass system unless sufficient propane is available in such systems. Indeed, applicant has found that propane gas can only significantly aid in removal of $CH_4$ and $CO_2$ from biomass systems when a continuously operating anaerobic digester is receiving (e.g., by sparging) propane gas in amounts such that the biogas product of the anaerobic digestion is comprised of at least 0.5 volume percent propane and more preferably when such propane gas is introduced into an anaerobic digester in concentrations such that the biogas contains from about 6.0 to about 15.0 volume percent propane.

Next, it should be noted that the higher BTU (British Thermal Units) biogases gases will result from introducing propane-containing stripper gases into an anaerobic digestion system. This facilitates use of the resulting propane "enriched" biogas gas mixture as a fuel. This follows from the fact that ordinary biogas (comprised chiefly of $CH_4$+ $CO_2$) has a BTU value of only about 650 BTU/ft$^3$. Hence, it is not a particularly good fuel in its own right. Consequently, if it is to be burned in its own right, burners and nozzles must be retrofitted to accommodate the burning of such low BTU gases. However, when a biogas contains approximately 10 volume percent propane, the BTU content of the resulting biogas will be increased to about 900 BTU/ft$^3$. This fuel value is such that the retrofitting that otherwise would be needed to burn ordinary biogas can be decreased or even eliminated.

The economic benefits of the herein described processes, also follow, in part, from decreased residence times in the reactor i.e., decreased solids retention time. Thus, by decreasing the solids retention time, the same volume anaerobic vessel will be able to process increased organic loads. Because anaerobic digesters currently cost approximately $2/gallon of capacity to construct, increasing their reaction rates and decreasing their solids retention time will result in significant economic savings. It also should be noted in passing that, because the propane gas can be introduced in an existing digester by sparging, or other means, low cost retrofit of existing digesters is a highly favored method of implementing the herein described processes.

In order to more fully establish the main concept of this invention (use of relatively large amounts of propane, i.e., larger than those "trace" amounts of propane that are "naturally" produced by a anaerobic digester) and the preferred operating parameters of using such propane (i.e., use of amounts of propane gas such that the biogas produced by the anaerobic digester is more than 0.5 volume percent and preferably between 6 and 15 volume percent) applicant conducted a series of experiments that are exemplified by the following examples.

EXAMPLE I

Two anaerobic digesters ($D_1$ and $D_2$) each having a 4.0 liter capacity and containing 2 liters of activated sewage sludge obtained from a municipal wastewater treatment plant (Boulder, Colo.) were equipped with pumps to achieve gas recirculation. One digester ($D_1$) was used as a control while the other ($D_2$) received propane according to the teachings of this patent disclosure. Each digester was fed with a 50 ml solution of water containing 4.0 gms of corn syrup. The resulting biogases were recirculated back into the liquid of the digester at the rate of 0.6 cubic feet/hour. In the propane-containing digester ($D_2$), a total of 12% propane was present in the recirculating gas. The experiment was run for a 24 hour period at steady state conditions. The organic loading of the digester was 2.0 gms volatile solids/liter/day. For every 50 ml of feed solution added, 50 ml of sludge was removed. Stirring of the digester was accomplished by sparging recirculating gases. Temperature was maintained at 37.0° C. Table I shows the rate of change of biogas production with, and without, propane being present. The results were as follows:

TABLE I

| | Rates of Biogas Production | |
|---|---|---|
| Time (min.) | D1 CONTROL (ml) | D2 PROPANE PRESENT (ml) |
| 15 | 105 | 200 |
| 30 | 290 | 485 |
| 60 | 560 | 800 |
| 130 | 830 | 1065 |
| 300 | 1230 | 1600 |
| 420 | 1300 | 1670 |
| 555 | 1485 | 1830 |
| 1440 | 1770 | 1900 |
| | pH 7.2 | pH 7.4 |

Comparing the rates of biogas production in Table I, the presence of propane resulted in 95 ml extra biogas being generated in the first 15 minutes and 195 ml extra biogas being generated in the first 30 minutes of feeding. Thus, the presence of propane resulted in a 90% faster utilization of the feed in the first 15 minutes, a 67% faster utilization in the first 30 minutes and a 28% faster utilization over a 7 hour period.

EXAMPLE II

Experimental conditions in Example II were the same as those for Example I except that only 3 gms of corn syrup were added as feed to each digester in 50 ml of solution (1.5 gms volatile solids/liter). The flow rate of recirculated gas was 0.4 cubic feet per hour. The propane content in D2 was approximately 9.0%. Table II shows the rate of biogas produced as a function of time with, and without, propane being present. The results of this experiment were as follows:

TABLE II

| | Rates of Biogas Production | |
|---|---|---|
| Time (min) | D1 CONTROL (ml) | D2 PROPANE PRESENT (ml) |
| 20 | 100 | 140 |
| 34 | 230 | 290 |
| 82 | 510 | 590 |
| 200 | 840 | 920 |
| 260 | 930 | 1030 |
| 360 | 1040 | 1180 |
| 1380 | 1740 | 1660 |
| | pH 7.2 | pH 7.3 |

The results of this experiment again show a faster utilization of feed when propane is present compared to a comparable system receiving no propane. As seen in Table II after 20 minutes 40 ml of additional biogas was produced when propane was present in the recirculated gas at a concentration of approximately 9.0%. An additional 60 ml or 26% more biogas was present after 34 minutes and 140 ml or 13% more biogas was present after 6 hours. This again shows that the presence of propane increases the rate of bacterial conversion of feed to biogas.

EXAMPLE III

Prior to the introduction of propane into the "D2" digester, it was run as a control for 10 days under the same experimental conditions (3.0 gms corn syrup feed) as in Example II except for the absence of propane. Rates of biogas production are shown in Table III below.

TABLE III

| | Rates of Biogas Production | |
|---|---|---|
| Time (min) | D1 CONTROL (ml) | D2 PROPANE PRESENT (ml) |
| 30 | 275 | 224 |
| 60 | 142 | 141 |
| 90 | 51 | 50 |
| 24 hrs. | 1340 | 1560 |

As seen in Table III the rate of biogas production for both digesters was essentially the same when no propane was present.

EXAMPLE IV

Evidence That Propane Is Not A Food Source

Four gms of corn syrup was added as feed to both digester $D_1$ (the unit receiving no propane) and to the second digester $D_2$. The propane concentration averaged 11% of the biogas volume. Numerous other tests (see Examples I and II) showed biogas production to be about 1700 ml±8% for a comparable system. Applicant reasons that, if propane was being consumed as a food source, the volumetric increase from propane conversion to methane (and carbon dioxide) would have resulted in the production of additional biogas beyond that due to the corn syrup feed. Thus, if propane were being used as a food source the total volume of biogas produced would far exceed the volume of biogas produced in the control (non-propane) digester since the D2 (propane) digester did not show any significant difference in total volume of biogas produced (but rather only in the rate of biogas production) (see Examples I and II) as compared to the D1 (control) digester, then no indication exists that the wastewater bacteria can use propane as a food source. In fact the experimental data strongly supports the conclusion wastewater bacteria can not use propane as a food source.

EXPERIMENTAL RESULTS

The conclusions that can be drawn from applicant's experimental program include the following.

1. The rate of biogas production is faster in a digester containing propane in the quantities taught by this patent disclosure compared to a digester that does not receive propane in such quantities. However, the total quantity of gas produced is essentially the same for both the digester receiving propane and the digester that did not receive propane.

2. Propane introduced into a digester having sufficient quantities of propane to produce applicant's desired propane concentrations in the biogas products of an anaerobic digester do not constitute a significant food source for bacteria common to wastewater treatment anaerobic digesters. This was evidenced by the fact that there was no increase in the total volume of the biogas (only an increase in rate of biogas production was observed).

3. The pH in the propane-receiving digester system was consistently about 0.1–0.2 pH units higher than that of the control digester. This is due to the fact that the $CO_2$ gas was stripped by the propane and, therefore, was not available for production of carbonic acid. Thus, smaller quantities of caustic (pH adjusting chemicals) will be required in applicant's propane receiving digester systems because they will naturally maintain a higher pH (a more preferred condition in such systems).

4. A faster rate of biogas production at the time of maximum feed introduction suggests the same volume capacity of a propane-receiving anaerobic digester vessel will be capable of processing a significantly greater amount of feed per unit time and per unit of digester volume.

5. The addition of propane to anaerobic digesters in quantities such that the biogas product contains at least one percent propane resulted in the observed increased rate of biogas production. For example, Example III shows essentially the same rates of biogas production in both digesters when propane is not present. This result should be compared to those of Examples I and II wherein the rate of biogas production is significantly faster after propane has been introduced.

6. These experiments indicate that applicant's processes effectively employ the law of mass action (Le Chattier's principle) by introducing relatively large quantities of propane into anaerobic digesters to aid in the stripping of low solubility gases such as methane out of an anaerobic biomass system. That is to say applicant's processes do not achieve appreciably higher methane production per unit of feed, but rather provide a faster kinetic reaction rate conversion per unit of feed. Indeed, applicant has found that the quantity of biogas produced by his processes will not produce greater total volumes of methane (biogas), but rather will allow a faster "rate" of methane production.

7. The hereindescribed processes can be improved by such optional procedures as (1) introducing anti-foaming agents known to this art into the biomass, (2) using slight vacuum conditions (e.g., 100 Torr) to remove biogas from the anaerobic digester system, (3) recycling a mixture of biogas produced by the anaerobic digestion process back into the biomass and (4) mixing biogas produced by the digestion with a portion of externally produced propane gas and recycling the resultant biogas/propane mixture back into the biomass.

DETAILED DESCRIPTION OF THE INVENTION

Figure 1:
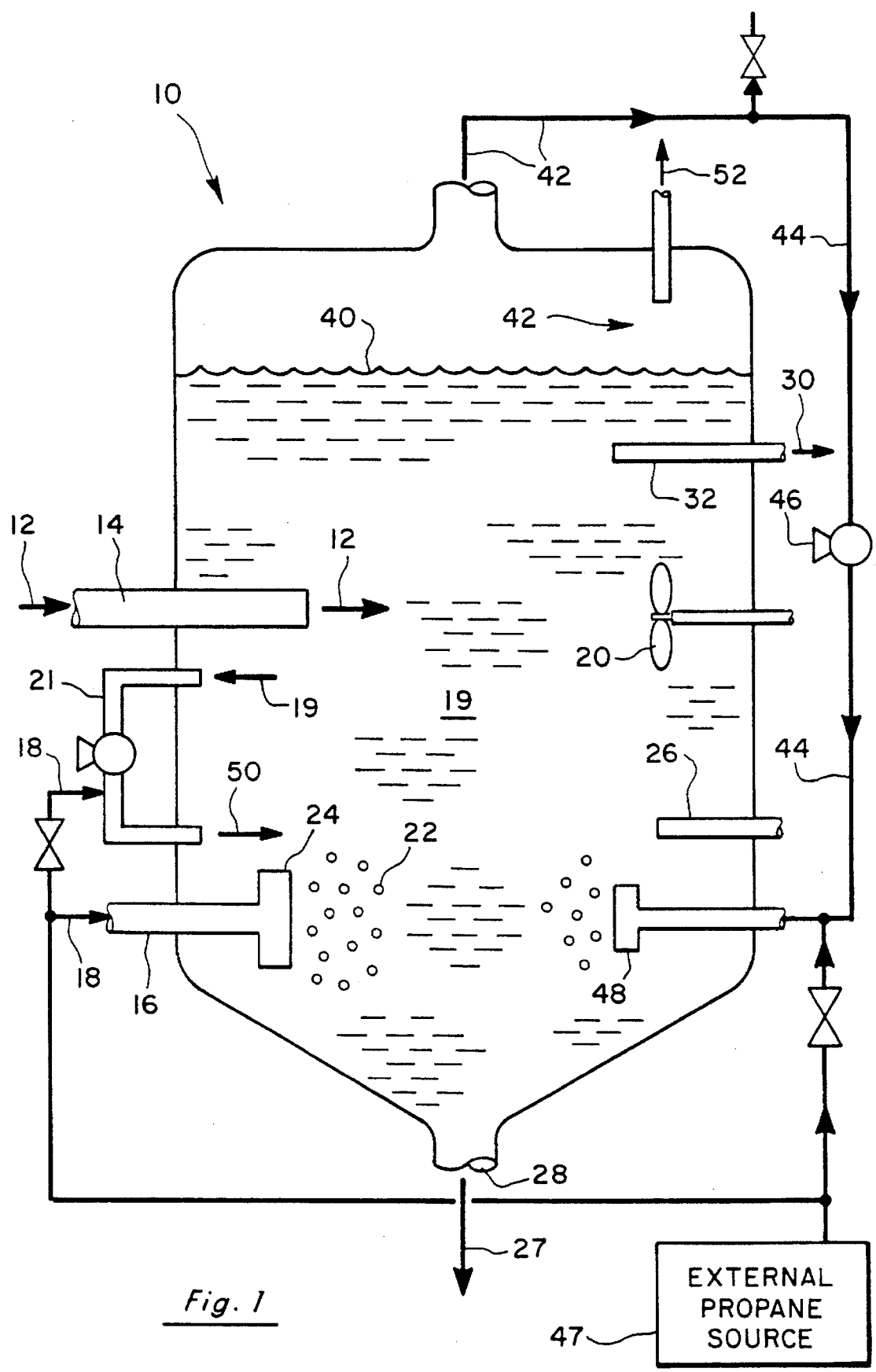
FIG. 1 depicts how the processes of this invention can be implemented by means of a single anaerobic digester/reactor unit. This single unit is shown by way of example only; those skilled in this art will readily appreciate that the herein described processes may be carried by multiple unit reactor systems—and/or easily retrofitted to a wide variety of existing anaerobic digesters.

FIG. 1 depicts an anaerobic digester 10 to which a wastewater feedstock to be treated is delivered, and from which various products of the anaerobic digestion are removed. The incoming wastewater feedstock 12 is shown being delivered to digester 10 via a feedstock conduit 14 shown located in a center portion of the digester 10. The level or position of this feedstock conduit 14 in the digester 10 can be varied greatly, but generally speaking this feedstock entry location is preferably above the entry level of the conduit 16 through which the propane-containing stripper gas 18 enters the digester 10. This propane-containing stripper gas 18 is obtained from a source external to the digester 10 (e.g., it can be obtained from propane storage tanks not shown in FIG. 1).

The biomass 19 within the digester 10 may be stirred by the sparging action of the incoming stripper gas 18 and, optionally, by mechanical stirring devices such as an impeller system 20 and/or by a fluid recirculation loop system 21. The average size of the propane-containing stripper gas bubbles 22 created by a sparging head 24 can be varied by means well known to this art, however, larger numbers of small diameter bubbles are generally preferable to smaller number of large diameter bubbles.

The digester 10 can be fitted and/or retrofitted with various fluid injection and ejection ports in order to control its operation. For example, inlet port 26 may be used to introduce such varied materials as fresh water, new microorganisms, microorganism nutrients and various other reagents such as antifoaming reagents and the like into the biomass 19. Similarly, various products of the anaerobic digestion taking place in digester 10 can be removed at any one or all of several places. For example heavier, sludge-like products 27 can be removed via a bottom drain port 28 as is generally suggested by the flow arrow shown there. Liquid products 30 may be removed through an exit pipe 32 in a higher region of the digester 10. Biogas products of the anaerobic digestion such as carbon dioxide and methane arising above the liquid level 40 of the biomass 19 will form a biogas 42. Sufficient amounts of propane-containing stripper gas 18 should be introduced into the biomass 19 such that the resulting biogas 42 will have a propane component that constitutes at least 0.5 percent by volume of said biogas 42.

Again, in the more preferred embodiments of this invention, sufficient propane-containing gas will be introduced into the biomass 19 such that the biogas 42 will be comprised of from about 6 to about 15 volume percent propane gas. This resulting biogas 42 may be employed as a fuel for utility purposes (local or long distant) and/or said propane-containing biogas 42 may be recycled as indicated by stream 44 back into the reactor via pumping system 46. This biogas 42 also can be mixed with additional propane from an external propane source 47 (external to this digester 10) and added to the recycled biogas stream 44 e.g., via a sparging systems 48.

FIG. 1 also depicts a particularly preferred method of introducing some of, or all of a propane-containing gas 18 into the biomass 19 by withdrawing some of the biomass 19 via liquid phase recirculation loop system 21 and mixing a portion of the liquid phase material passing through the recirculation loop system 21 with a propane-containing gas 18 and introducing the resulting mixture 50 back into biomass 19. As a final note, it also should be noted that slight negative pressures (e.g., 100 Torr) may be maintained over the liquid level 40 by vacuum producing means 52 not shown but well known to this art.

Thus, while applicant's invention has been described with respect to various scientific theories, and a spirit which is committed to the concept of introducing pure propane and/or a propane-containing gas mixture into a biomass undergoing anaerobic digestion in order to strip biogas from the system more efficiently, it is to be understood that this invention is not limited thereto; but rather only should be limited by the scope of the following claims.

Thus, having disclosed this invention, what is claimed is:

1. A process for an anaerobic digestion of an organic material-containing wastewater, said process comprising introducing a propane-containing gas, obtained from a source other than the anaerobic digestion, into a biomass containing said wastewater in an amount such that a propane gas component of a biogas produced by the anaerobic digestion is at least 3.0 percent by volume of said biogas.

2. The process of claim 1 wherein the propane gas component of the biogas is from about 6 to about 15 volume percent of said biogas.

3. The process of claim 1 wherein the propane-containing gas is bottled propane gas.

4. The process of claim 1 wherein the propane-containing gas is a liquid propane gas that is introduced into the biomass in a liquid state and which, thereupon, flashes into a gaseous state.

5. The process of claim 1 wherein the propane-containing gas is an industrial byproduct gas.

6. The process of claim 1 wherein the propane-containing gas is sparged into the biomass.

7. The process of claim 1 wherein the biomass additionally comprises an antifoaming agent.

8. The process of claim 1 wherein a slight negative pressure is applied above the biomass to aid in more rapid removal of the propane-containing biogas.

9. The process of claim 1 that additionally comprises the step of recycling biogas produced by the anaerobic digestion back into the biomass.

10. The process of claim 1 that additionally comprises the step of recycling biogas produced by the process and a propane-containing gas from an external source back into the biomass.

11. The process of claim 1 that additionally comprises the step of injecting a propane-containing gas from an external source into a digester liquid that is being withdrawn from the digester and then pumped back into said digester.

12. The process of claim 1 that additionally comprises retrofitting an existing digester to carry out the process of claim 1.

13. The process of claim 1 wherein the biogas produced by the anaerobic digestion is used as a fuel.

* * * * *